US010850017B2

(12) United States Patent
Fulkerson et al.

(10) Patent No.: US 10,850,017 B2
(45) Date of Patent: Dec. 1, 2020

(54) METHODS AND SYSTEMS FOR DETECTING AN OCCLUSION IN A BLOOD CIRCUIT OF A DIALYSIS SYSTEM

(71) Applicant: Fresenius Medical Care Holdings, Inc., Waltham, MA (US)

(72) Inventors: Barry Neil Fulkerson, Longmont, CO (US); Nhan Viet Pham, Fountain Valley, CA (US); Alec Huang, Irvine, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 21 days.

(21) Appl. No.: 16/232,590

(22) Filed: Dec. 26, 2018

(65) Prior Publication Data

US 2019/0381228 A1    Dec. 19, 2019

Related U.S. Application Data

(63) Continuation of application No. 15/453,855, filed on Mar. 8, 2017, now Pat. No. 10,195,326.

(Continued)

(51) Int. Cl.
*A61M 1/16*  (2006.01)
*A61M 1/36*  (2006.01)
(Continued)

(52) U.S. Cl.
CPC ............ *A61M 1/1601* (2014.02); *A61M 1/14* (2013.01); *A61M 1/267* (2014.02); *A61M 1/34* (2013.01);
(Continued)

(58) Field of Classification Search
CPC ...... A61M 1/14; A61M 1/1601; A61M 1/267; A61M 1/34; A61M 1/3626; A61M 1/3693;
(Continued)

(56) References Cited

U.S. PATENT DOCUMENTS 3,242,456 A    3/1966  Duncan
3,803,913 A    4/1974  Tracer
(Continued)

FOREIGN PATENT DOCUMENTS

JP    2002139165 A    5/2002
WO    20015069412 A1    7/2001
(Continued)

OTHER PUBLICATIONS

International Search Report for PCT/US17/21456, dated Jun. 21, 2017.

*Primary Examiner* — Patrick Orme
(74) *Attorney, Agent, or Firm* — Novel IP (57) ABSTRACT

The present specification describes systems and methods for detecting an occlusion in a tubing carrying a patient's blood through a manifold and into a dialyzer in a dialysis system. A controller measures pressures value of the blood at a predetermined point after exiting the manifold and before entering the dialyzer, calculates a historical running average, calculates a weighted sum of the most recent pressure values, and determines whether to trigger an occlusion alarm based on a function of the historical running average and the weighted sum of the most recent pressure values.

20 Claims, 10 Drawing Sheets

Related U.S. Application Data (60) Provisional application No. 62/305,212, filed on Mar. 8, 2016.

(51) Int. Cl.
*A61M 1/14* (2006.01)
*A61M 1/26* (2006.01)
*A61M 1/34* (2006.01)

(52) U.S. Cl.
CPC ....... *A61M 1/3626* (2013.01); *A61M 2205/12* (2013.01); *A61M 2205/15* (2013.01); *A61M 2205/18* (2013.01); *A61M 2205/3331* (2013.01); *A61M 2205/3337* (2013.01); *A61M 2205/3393* (2013.01); *A61M 2205/50* (2013.01); *A61M 2205/52* (2013.01); *A61M 2205/6072* (2013.01)

(58) Field of Classification Search
CPC .......... A61M 2205/12; A61M 2205/15; A61M 2205/18; A61M 2205/52; A61M 2205/50; A61M 2205/3331; A61M 2205/3393; A61M 2205/3337; A61M 2205/6072; A61M 5/15854; A61M 2005/16863; A61M 2005/16868; G01L 19/12
See application file for complete search history.

(56) References Cited

U.S. PATENT DOCUMENTS

| | | | |
|---|---|---|---|
| 3,961,918 A | 6/1976 | Johnson | |
| 3,989,625 A | 11/1976 | Mason | |
| 4,354,562 A | 10/1982 | Newman | |
| 4,397,519 A | 8/1983 | Cooney | |
| 4,403,765 A | 9/1983 | Fisher | |
| 4,430,098 A | 2/1984 | Bowman | |
| 4,480,483 A | 11/1984 | McShane | |
| 4,531,799 A | 7/1985 | Gray | |
| 4,535,637 A | 8/1985 | Feller | |
| 4,586,576 A | 5/1986 | Inoue | |
| 4,740,755 A | 4/1988 | Ogawa | |
| 4,828,543 A | 5/1989 | Weiss | |
| 5,000,274 A | 3/1991 | Bullivant | |
| 5,074,368 A | 12/1991 | Bullivant | |
| 5,114,580 A | 5/1992 | Ahmad | |
| 5,170,789 A | 12/1992 | Narayan | |
| 5,228,308 A | 7/1993 | Day | |
| 5,258,127 A | 11/1993 | Gsell | |
| 5,476,592 A | 12/1995 | Simard | |
| 5,725,776 A | 3/1998 | Kenley | |
| 5,782,796 A | 7/1998 | Din | |
| 5,915,932 A | 6/1999 | Nabity | |
| 5,954,971 A | 9/1999 | Pages | |
| 5,989,438 A | 11/1999 | Fumiyama | |
| 6,044,691 A | 4/2000 | Kenley | |
| 6,358,225 B1 | 3/2002 | Butterfield | |
| 6,487,904 B1 | 12/2002 | Myhre | |
| 6,491,656 B1 | 12/2002 | Morris | |
| 6,638,478 B1 | 10/2003 | Treu | |
| 6,653,841 B1 | 11/2003 | Koerdt | |
| 6,681,624 B2 | 1/2004 | Furuki | |
| 6,691,047 B1 | 2/2004 | Fredericks | |
| 6,752,172 B2 | 6/2004 | Lauer | |
| 6,836,201 B1 | 12/2004 | Devenyi | |
| 6,948,697 B2 | 9/2005 | Herbert | |
| 7,087,026 B2 | 8/2006 | Callister | |
| 7,097,148 B2 | 8/2006 | DeWall | |
| 7,270,015 B1 | 9/2007 | Feller | |
| 7,387,022 B1 | 6/2008 | Korniyenko | |
| 8,040,493 B2 | 10/2011 | Fulkerson | |
| 8,105,487 B2 | 1/2012 | Fulkerson | |
| 8,114,288 B2 | 2/2012 | Robinson | |
| 8,137,553 B2 | 3/2012 | Fulkerson | |
| 8,240,636 B2 | 8/2012 | Smith | |
| 8,395,761 B2 | 3/2013 | Fulkerson | |
| 8,475,399 B2 | 7/2013 | Fulkerson | |
| 8,535,522 B2 | 9/2013 | Fulkerson | |
| 8,597,505 B2 | 12/2013 | Fulkerson | |
| 8,771,511 B2 | 7/2014 | Robinson | |
| 9,157,786 B2 | 10/2015 | Fulkerson | |
| 9,199,022 B2 | 12/2015 | Fulkerson | |
| 9,201,036 B2 | 12/2015 | Fulkerson | |
| 9,295,772 B2 | 3/2016 | Fulkerson | |
| 9,308,307 B2 | 4/2016 | Fulkerson | |
| 9,352,282 B2 | 5/2016 | Fulkerson | |
| 9,354,640 B2 | 5/2016 | Byler | |
| 9,358,331 B2 | 6/2016 | Fulkerson | |
| 9,360,129 B2 | 6/2016 | Smith | |
| 9,415,152 B2 | 8/2016 | Robinson | |
| 9,517,296 B2 | 12/2016 | Fulkerson | |
| 9,759,710 B2 | 9/2017 | Fulkerson | |
| 10,195,326 B2 * | 2/2019 | Fulkerson | A61M 1/3626 |
| 2002/0094927 A1 | 7/2002 | Odak | |
| 2002/0151804 A1 | 10/2002 | O'Mahony | |
| 2002/0158019 A1 | 10/2002 | Collins | |
| 2003/0048185 A1 | 3/2003 | Citrenbaum | |
| 2003/0056585 A1 | 3/2003 | Furuki | |
| 2003/0220598 A1 | 11/2003 | Busby | |
| 2004/0031756 A1 | 2/2004 | Suzuki | |
| 2005/0086008 A1 | 4/2005 | DiGianfilippo | |
| 2005/0101901 A1 | 5/2005 | Gura | |
| 2005/0131332 A1 | 6/2005 | Kelly | |
| 2005/0133439 A1 | 6/2005 | Blickhan | |
| 2006/0195064 A1 | 8/2006 | Plahey | |
| 2006/0226057 A1 | 10/2006 | Robinson | |
| 2006/0289342 A1 | 12/2006 | Sugioka | |
| 2007/0112297 A1 | 5/2007 | Plahey | |
| 2007/0179425 A1 | 8/2007 | Gura | |
| 2007/0253463 A1 | 11/2007 | Perry | |
| 2007/0269340 A1 | 11/2007 | Dannenmaier | |
| 2008/0041792 A1 | 2/2008 | Crnkovich | |
| 2008/0214979 A1 | 9/2008 | Brugger | |
| 2008/0230450 A1 | 9/2008 | Burbank | |
| 2008/0258735 A1 | 10/2008 | Quackenbush | |
| 2008/0290974 A1 | 11/2008 | Adams | |
| 2009/0008306 A1 | 1/2009 | Cicchello | |
| 2009/0101549 A1 | 4/2009 | Kamen | |
| 2009/0101552 A1 | 4/2009 | Fulkerson | |
| 2009/0101577 A1 | 4/2009 | Fulkerson | |
| 2009/0127193 A1 | 5/2009 | Updyke | |
| 2010/0129247 A1 | 5/2010 | Lauer | |
| 2010/0140149 A1 | 6/2010 | Fulkerson | |
| 2010/0331754 A1 | 12/2010 | Fulkerson | |
| 2011/0054378 A1 | 3/2011 | Fulkerson | |
| 2011/0071465 A1 | 3/2011 | Wang | |
| 2011/0303598 A1 | 12/2011 | Lo | |
| 2011/0315611 A1 | 12/2011 | Fulkerson | |
| 2012/0214117 A1 | 8/2012 | Broker | |
| 2013/0020237 A1 | 1/2013 | Wilt | |
| 2013/0220907 A1 | 8/2013 | Fulkerson | |
| 2013/0280104 A1 | 10/2013 | Heide | |
| 2014/0094732 A1 | 4/2014 | Bernard | |
| 2014/0188040 A1 | 7/2014 | Busby | |
| 2014/0276537 A1 | 9/2014 | Kruse | |
| 2015/0258263 A1 | 9/2015 | Hogard | |
| 2015/0314055 A1 | 11/2015 | Hogard | |
| 2016/0069732 A1 | 3/2016 | Fulkerson | |
| 2016/0109398 A1 | 4/2016 | Fulkerson | |
| 2016/0317733 A1 | 11/2016 | Fulkerson | |
| 2016/0319954 A1 | 11/2016 | Smith | |
| 2017/0007756 A1 | 1/2017 | Robinson | |
| 2017/0021085 A1 | 1/2017 | Fulkerson | |
| 2017/0021088 A1 | 1/2017 | Fulkerson | |
| 2017/0021306 A1 | 1/2017 | Fulkerson | |
| 2017/0023953 A1 | 1/2017 | Byler | |
| 2017/0232177 A1 | 8/2017 | Fulkerson | |

FOREIGN PATENT DOCUMENTS

| | | |
|---|---|---|
| WO | 2009073567 | 6/2009 |
| WO | 2010042666 | 4/2010 |
| WO | 2010062698 | 6/2010 |
| WO | 2010081121 | 7/2010 |

(56) References Cited

FOREIGN PATENT DOCUMENTS

| WO | 2012108910 | 8/2012 |
|---|---|---|
| WO | 2014105267 A1 | 7/2014 |
| WO | 2014105755 | 7/2014 |
| WO | 2014161008 | 10/2014 |
| WO | 2017106356 A1 | 6/2017 |

* cited by examiner

METHODS AND SYSTEMS FOR DETECTING AN OCCLUSION IN A BLOOD CIRCUIT OF A DIALYSIS SYSTEM

CROSS-REFERENCE

The present application is a continuation application of U.S. patent application Ser. No. 15/453,855, entitled "Methods and Systems for Detecting an Occlusion in a Blood Circuit of a Dialysis System" and filed on Mar. 8, 2017, which relies on U.S. Patent Provisional No. 62/305,212, titled "Method for Detecting Occlusion in a Portable Hemodialysis Circuit" and filed on Mar. 8, 2016, for priority. The aforementioned applications are incorporated herein by reference in their entirety.

FIELD

The present specification discloses a dialysis system with improved occlusion detection functionality. In particular, the disclosed dialysis system includes an occlusion detector for detecting occlusions in a blood circuit with improved accuracy and lower false positive alarms.

BACKGROUND

Blood purification systems, which are used for conducting hemodialysis, hemodiafiltration or hemofiltration, involve the extracorporeal circulation of blood through an exchanger having a semi-permeable membrane. Such systems further include a hydraulic system for circulating blood and a hydraulic system for circulating replacement fluid or dialysate comprising certain blood electrolytes in concentrations close to those of the blood of a healthy subject.

A common problem with all dialysis systems is the accurate detection, and alarming of, an occlusion. In the course of a dialysis treatment, blood is extracted from a patient, through a blood flow circuit that contains a dialyzer, and back to the patient. Flow through the blood circuit may, at times, become occluded by an increased concentration of gasses, coagulation, or various other blood components. An occlusion not only inhibits effective dialysis but can also be dangerous if not detected immediately and cleared.

In cases of an occlusion in the arterial line, or blood circuit, transporting a patient's blood to a dialyzer, an accumulation of gasses may lead to the formation of bubbles. U.S. Pat. No. 9,320,843 discloses "a device for monitoring an extracorporeal blood circuit in which a blood pump is disposed to convey blood, comprising: an apparatus adapted to detect an occurrence of air bubbles in blood that flows in the extracorporeal blood circuit, an apparatus adapted to measure a negative pressure in the extracorporeal blood circuit upstream of the blood pump, and a processing unit programmed to deduce a first defective condition when the apparatus adapted to detect the occurrence of air bubbles in the extracorporeal blood circuit detects air bubbles and the measured negative pressure is above a predetermined limit value for the negative pressure, and/or a second defective condition when the apparatus adapted to detect the occurrence of air bubbles in the extracorporeal blood circuit detects air bubbles and the measured negative pressure is below the predetermined limit value for the negative pressure, wherein the first defective condition differs from the second defective condition."

U.S. Pat. No. 8,465,641 discloses "a dialysis liquid circuit comprising: conduits for conducting a dialysis liquid, and elements for continuously detecting air in the dialysis liquid and leakage in the dialysis liquid circuit, the elements including at least one gas sensor traversed continuously by dialysis liquid, the at least one gas sensor being configured such that it measures at least one property of the dialysis liquid which depends on the presence of air bubbles in the dialysis liquid, and being arranged downstream of a region to be monitored of the dialysis liquid circuit in which during operation of the dialysis liquid circuit a negative pressure exists with respect to atmospheric pressure, and an evaluation unit which is connected with the gas sensor and is configured such that the property measured via the gas sensor is evaluated with regard to the presence of air bubbles in the dialysis liquid and based thereon, with regard to the presence of leakage in the dialysis liquid circuit."

While prior art systems have used pressure sensors to generally detect pressure changes and generate alarms or shut down dialysis procedures, they still suffer from excessively high false alarm rates. There remains a need for an improved occlusion detector that can reliably detect an occlusion in a blood circuit but not falsely alarm and unnecessarily cause a dialysis treatment to prematurely terminate.

SUMMARY

The present specification discloses a dialysis system comprising: a manifold comprising an enclosed blood flow path, wherein said blood flow path comprises a blood inlet port, a blood outlet port, and a flexible tube positioned between said blood inlet port and blood outlet port; a pressure sensor in physical communication with manifold at a position proximate said blood outlet port; a non-transient memory in data communication with said pressure sensor and configured to store pressure values generated and transmitted by said pressure sensor; at least one pump in physical contact with said flexible tube and configured to pump blood from a patient's body, through a tube, and through said blood flow path; and a controller in data communication with said pressure sensor, said non-transient memory, and said at least one pump, wherein said controller is configured to execute a plurality of programmatic instructions in order to: receive said pressure values; determine an average of n pressure values, where n is a subset of said pressure values; determine a sum of m pressure values, where m is a subset of said pressure values and where m<n; apply a function of said average of n pressure values and said sum of m pressure values to generate an occlusion indicator value; and based upon said pressure difference value, determine if an alarm should be triggered.

Optionally, the dialysis system further comprises a housing that encloses said controller, the at least one pump, and the pressure sensor, wherein said housing is adapted to detachably receive said manifold.

Optionally, the dialysis system further comprises a dialyzer in fluid communication with the blood output port of said manifold. The pressure sensor may be positioned between the blood outlet port and the dialyzer.

Optionally, n is in a range of 10 to 20 pressure values.

Optionally, m is in a range of 3 to 10 pressure values.

Pressure values in the sum of m pressure values may include pressure values that are more recent than pressure values in the average of n pressure values.

Pressure values in the m subset of pressure values may include pressure values sensed later in time than pressure values in the n subset of pressure values.

Optionally, said controller is configured to execute a plurality of programmatic instructions in order to apply a weight to said average of n pressure values. The weight may be in a range of 3 to 10.

Optionally, said controller is configured to execute a plurality of programmatic instructions in order to apply a weight to each pressure value in said sum of m pressure values. The weight may be in a range of 1 to 5.

Optionally, said function takes a difference between said average of n pressure values and said sum of m pressure values to generate the occlusion indicator value. Optionally, said controller is configured to determine an alarm should be triggered when said occlusion indicator value is greater than or equal to a predefined threshold number. The predefined threshold number may be in a range of 200 to 450 mmHg. Optionally, said controller is configured to determine an alarm should be triggered when said occlusion indicator value is less than or equal to a predefined threshold number. The predefined threshold number may be in a range of 200 to 450 mmHg.

The present specification also discloses a dialysis system comprising: a manifold comprising an enclosed blood flow path, wherein said blood flow path comprises a blood inlet port, a blood outlet port, and a flexible tube positioned between said blood inlet port and blood outlet port; a pressure sensor in physical communication with manifold at a position proximate said blood outlet port; a non-transient memory in data communication with said pressure sensor and configured to store pressure values generated and transmitted by said pressure sensor; at least one pump in physical contact with said flexible tube and configured to pump blood from a patient's body, through a tube, and through said blood flow path; and a controller in data communication with said pressure sensor, said non-transient memory, and said at least one pump, wherein said controller is configured to execute a plurality of programmatic instructions in order to: receive said pressure values; determine an average of n pressure values, where n is a subset of said pressure values; determine a sum of m pressure values, where m is a subset of said pressure values, m<n, and pressure values in the m subset of pressure values include pressure values sensed later in time than pressure values in the n subset of pressure values; obtain a difference of said average of n pressure values and said sum of m pressure values to generate an occlusion indicator value;

compare said occlusion indicator value to a predefined threshold number; and based upon said comparison, determine if an alarm should be triggered.

Optionally, the dialysis system further comprises a housing that encloses said controller, the at least one pump, and the pressure sensor, wherein said housing is adapted to detachably receive said manifold wherein upon inserting and installing said manifold and closing said housing, said at least one pump is placed into physical contact with the flexible tube.

Optionally, the dialysis system further comprises a dialyzer in fluid communication with the blood output port of said manifold, wherein the pressure sensor is positioned between the blood outlet port and the dialyzer.

Optionally, n is in a range of 10 to 20 pressure values.

Optionally, m is in a range of 3 to 10 pressure values.

Optionally, said controller is configured to execute a plurality of programmatic instructions in order to apply a weight to said average of n pressure values. The weight may be in a range of 3 to 10. Optionally, said controller is configured to execute a plurality of programmatic instructions in order to apply a weight to each pressure value in said sum of m pressure values. The weight may be in a range of 1 to 5.

Optionally, said predefined threshold number is in a range of 200 to 450 mmHg.

Optionally, said predefined threshold number is 325 mmHg.

At least five pressure values in the m subset of pressure values may include pressure values sensed later in time than pressure values in the n subset of pressure values.

Optionally, said controller is configured to execute a plurality of programmatic instructions in order to determine if a dialysis process should be suspended or terminated based upon said comparison.

The aforementioned and other implementations of the present specification shall be described in greater depth in the drawings and detailed description provided below.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

While the present invention may be embodied in many different forms, for the purpose of promoting an understanding of the principles of the invention, reference will now be made to the implementations illustrated in the drawings and specific language will be used to describe the same. It will nevertheless be understood that no limitation of the scope of the invention is thereby intended. Any alterations and further modifications in the described implementations, and any further applications of the principles of the invention as described herein are contemplated as would normally occur to one skilled in the art to which the invention relates.

The term "and/or" means one or all of the listed elements or a combination of any two or more of the listed elements.

The terms "comprises", "includes", and variations thereof do not have a limiting meaning where these terms appear in the description and claims.

Unless otherwise specified, "a", "an", "the", "one or more", and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The present specification is directed towards multiple implementations. The following disclosure is provided in order to enable a person having ordinary skill in the art to practice the invention. Language used in this specification should not be interpreted as a general disavowal of any one specific implementation or used to limit the claims beyond the meaning of the terms used therein. The general principles defined herein may be applied to other implementations and applications without departing from the spirit and scope of the invention. Also, the terminology and phraseology used is for the purpose of describing exemplary implementations and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific implementation may be used and implemented with any other implementation unless clearly indicated otherwise.

Figure 1:
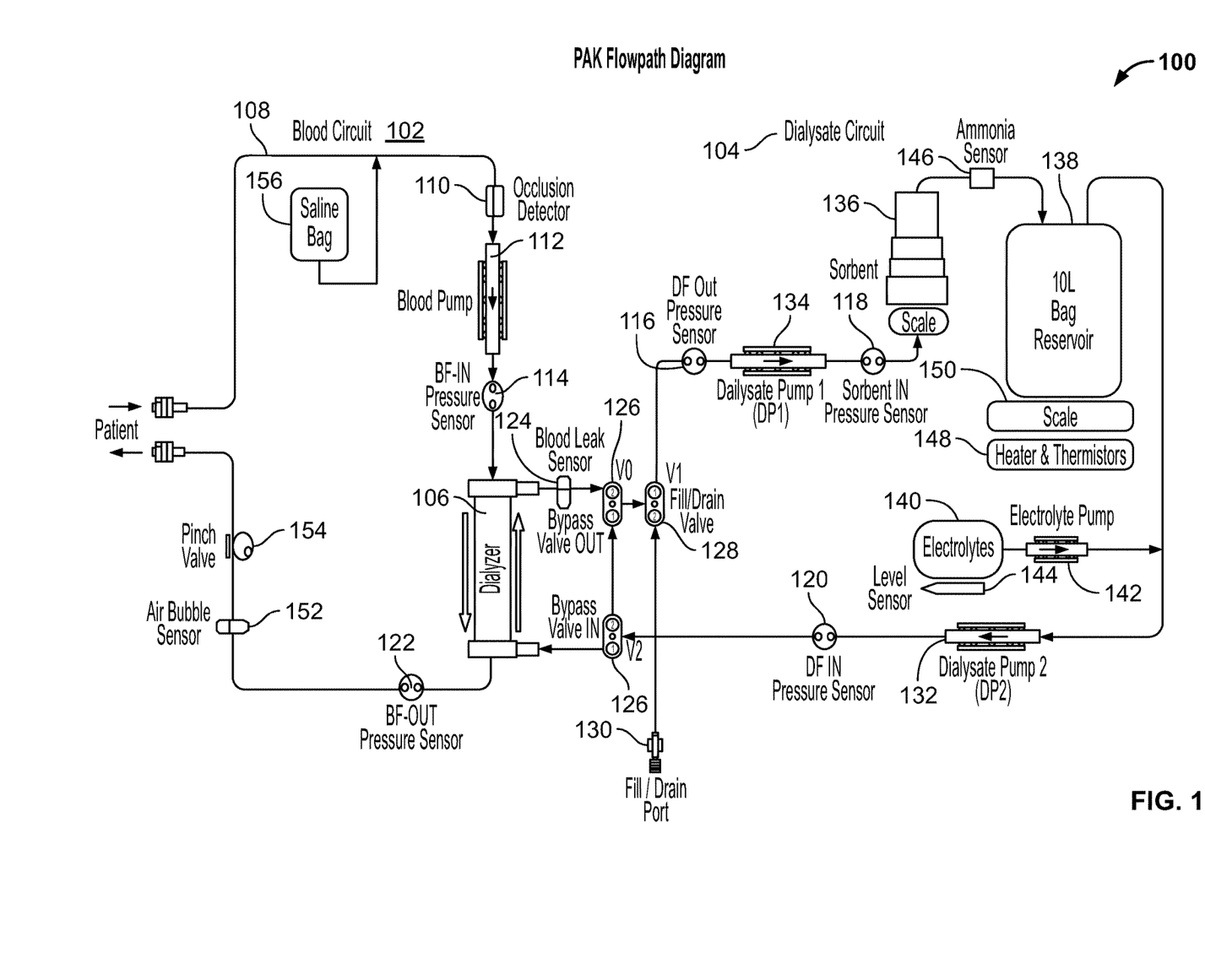
FIG. 1 illustrates the fluidic circuit for an extracorporeal blood processing system used for conducting hemodialysis and hemofiltration according to some implementations of the present specification.

Reference is now made to FIG. 1, which illustrates the fluidic circuit for an extracorporeal blood processing system 100 used for conducting hemodialysis and hemofiltration. In one implementation of the present invention, the system 100 is implemented as a portable dialysis system which may be used by a patient for conducting dialysis at home. The hemodialysis system includes two circuits: a blood circuit 102 and a dialysate circuit 104. Blood treatment during dialysis involves extracorporeal circulation through an exchanger having a semi permeable membrane: the hemodialyzer or dialyzer 106. The patient's blood is circulated in the blood circuit 102 on one side of the membrane (dialyzer) 106 and the dialysate, comprising the main electrolytes of the blood in concentrations prescribed by a physician, is circulated on the other side in the dialysate circuit 104. The circulation of dialysate fluid thus provides for the regulation and adjustment of the electrolytic concentration in blood.

The line 108 from the patient, which transports impure blood to the dialyzer 106 in the blood circuit 102 is provided with an occlusion detector 110, as further described below, which is generally linked to a visual or audible alarm to signal any obstruction to the blood flow. In an implementation, in order to prevent coagulation of blood, delivery means, such as a pump, syringe, or any other injection device, for injecting an anticoagulant—such as heparin, into blood may also be provided. A peristaltic pump 112 is also provided to ensure flow of blood in the normal (desired) direction.

A pressure sensor 114 is provided at, or proximate to, the inlet where impure blood enters the dialyzer 106. Other pressure sensors 116, 118, 120 and 122 are provided at various positions in the hemodialysis system to track and maintain fluid pressure at desired levels at specific points within the respective circuits.

At the point where used dialysate fluid from the dialyzer 106 enters the dialysate circuit 104, a blood leak sensor 124 is provided to sense and warn of any leakage of blood cells into the dialysate circuit. A pair of bypass valves 126 is also provided at the beginning and end points of the dialysate circuit, so that under conditions of start-up, or at other times as deemed necessary by the operator, the dialyzer can be bypassed from the dialysate fluid flow, yet the dialysate fluid flow can still be maintained, i.e. for flushing or priming operations. Another valve 128 is provided just before a priming/drain port 130. The port 130 is used for initially filling the circuit with a dialysate solution, and to remove used dialysate fluid after, and in some instances during, dialysis. During dialysis, valve 128 may be used to replace portions of used dialysate with high concentrations of, for instance, sodium with replenishment fluid of appropriate concentration so that overall component concentration of the dialysate is maintained at a desired level.

The dialysate circuit is provided with two peristaltic pumps 132 and 134. Pump 132 is used for pumping dialysate fluid to the drain or waste container, as well as for pumping regenerated dialysate into the dialyzer 106. Pump 134 is used for pumping out spent dialysate from the dialyzer 106, maintaining fluid pressure through the sorbent 136, and pumping in dialysis fluid from port 130 to fill the system or maintain component concentration in the dialysate.

A sorbent cartridge 136 is provided in the dialysate circuit 104. The sorbent cartridge 136 contains several layers of materials, each having a role in removing impurities, such as urea and creatinine. The combination of these layered materials allows water suitable for drinking to be charged into the system for use as dialysate fluid. It also allows closed loop dialysis. That is, the sorbent cartridge 136 enables regeneration of fresh dialysate from the spent dialysate coming from the dialyzer 106. For the fresh dialysate fluid, a lined container or reservoir 138 of a suitable capacity such as 0.5, 1, 5, 8 or 10 liters is provided.

Depending upon patient requirements and based on a physician's prescription, desired quantities of an infusate solution 140 can be added to the dialysis fluid. Infusate 140 is a solution containing minerals and/or glucose that help replenish minerals like potassium and calcium in the dialysate fluid at levels after undesired removal by the sorbent. A peristaltic pump 142 is provided to pump the desired amount of infusate solution 140 to the container 138. Alternatively, the infusate solution 140 can be pumped into the outflow line from reservoir 138. A camera 144 may optionally be provided to monitor the changing liquid level of the infusate solution as a safety check warning of infusate flow failure and/or function as a bar code sensor to scan bar codes associated with additives to be used in a dialysis procedure. Optionally, an ammonia sensor 146 may be provided.

A heater 148 is provided to maintain the temperature of dialysate fluid in the container 138 at the required level. The container 138 is also equipped with a scale 150 for keeping track of the weight, and therefore volume, of the fluid in the container 138.

An air (or bubble) sensor 152 and a pinch clamp 154 are employed in the circuit to detect and prevent any air, gas or gas bubbles from being returned to the patient.

A saline bag 156 is provided for filling the blood circuit 102 with sterile saline before it is used for dialysis.

If implemented in a conventional manner, the system would manifest as a mesh of tubing and would be too complicated for a home dialysis user to configure and use. Therefore, in order to make the system simple and easy to use at home by a patient, implementations of the present invention embody the fluidic circuits in the form of a compact manifold in which most components of the fluidic circuit are integrated into a single piece of molded plastic or multiple pieces of molded plastic that are configured to connect together to form a single operative manifold structure. In various implementations a manifold is used to minimize the risk of blood clotting, and eliminate air-blood interfaces for receiving an injection or administration of an anticoagulant. In one implementation, the manifold of the present invention includes a composite plastic manifold, into which the blood and dialysate flow paths are molded. Blood purification system components, such as sensors and pumps, are placed into pressure, thermal, and/or optical communication within the fluid flow contained within the molded manifold.

Figure 2:
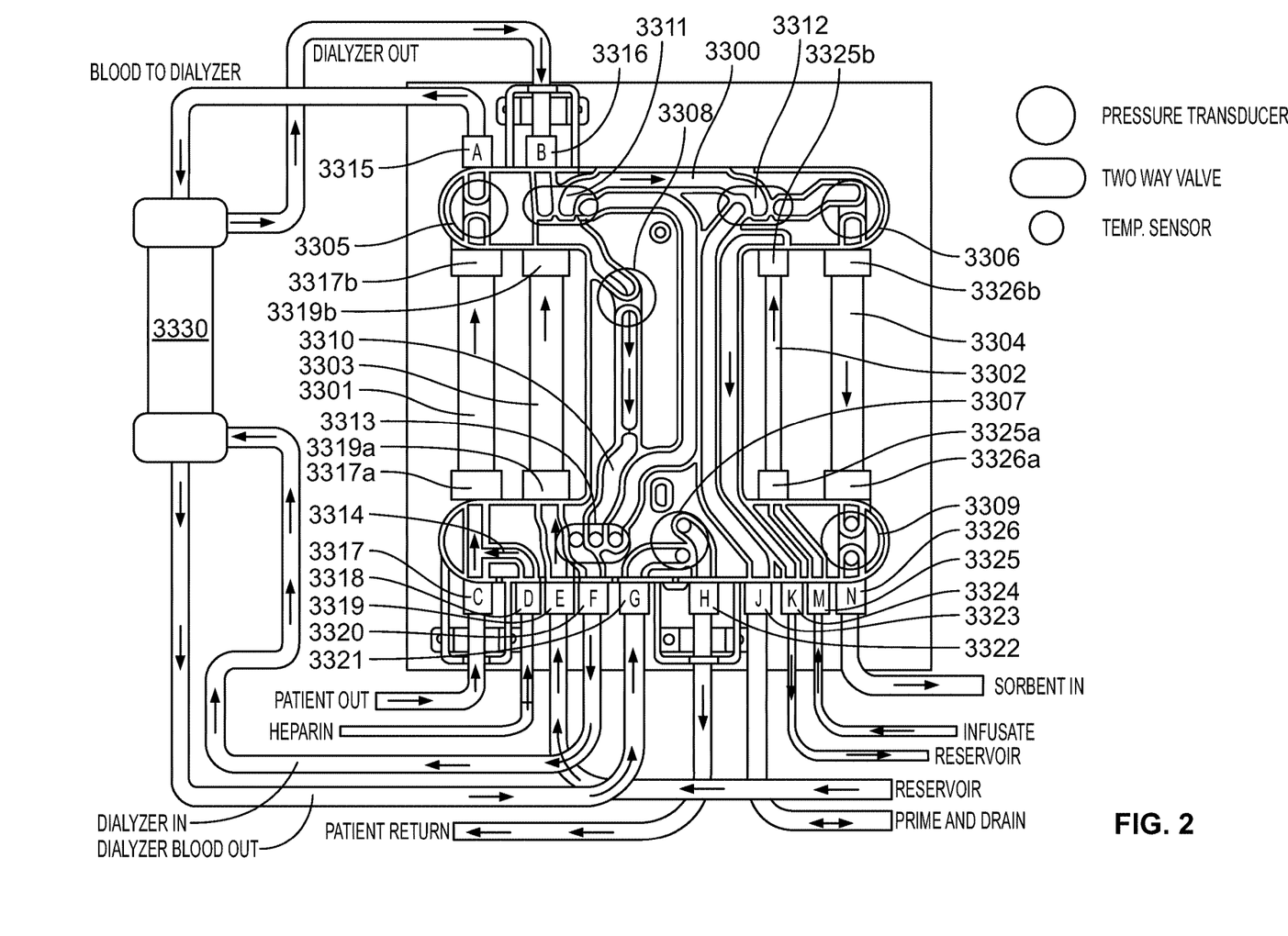
FIG. 2 is a diagram detailing the fluidic circuit for a compact manifold according to one implementation of the present specification.

FIG. 2 is a diagram of the fluidic circuit for the compact manifold according to one implementation of the present specification. The fluidic circuit includes four pump tube segments P1 3301, P2 3302, P3 3303 and P4 3304 in pressure communication with pumps within the top controller unit and pump shoes in the top controller unit door. It further includes five pressure membranes in pressure communication with pressure transducers or sensors 3305, 3306, 3307, 3308 and 3309, and an area in thermal or optical communication with a temperature sensor 3310. In the implementation illustrated in FIG. 2, three two-way valves 3311, 3312 and 3313, each comprising a pair of membranes, are integrated into the manifold. The two-way valves function as valves when they are occluded by a pin, member or protrusion from the controller unit.

Grouped in this manner the pairs of membranes form three two-way valves 3311, 3312, 3313. The two-way valves provide greater flexibility in controlling the configuration of a circuit. When conventional two-way valves are used to occlude portions of a fluid pathway, they are typically configured to enable two different fluid pathways, one for a first valve state and one for the second valve state. Certain valve implementations, as disclosed below, used in combination with the valve membranes or pressure points integrated into the manifold, enable more nuanced control, enabling the creation of four distinctly different fluid flow paths.

Pump tube segments 3301, 3302, 3303, 3304 are bonded into the compact manifold. A number of ports are provided in the manifold, which connect with tubes external to the manifold to allow the flow of various fluids in and out of the manifold. These ports are connected to various tubes in the blood purification system for carrying fluids as follows:

Port A 3315—blood to the dialyzer 3330;
Port B 3316—dialyzer output (used dialysate);
Port C 3317—blood from the patient;
Port D 3318—heparin for mixing in the blood;
Port E 3319—reservoir output (fresh dialysate);
Port F 3320—dialyzer input (fresh dialysate);
Port G 3321—dialyzer output (blood);
Port H 3322—patient return (clean blood);
Port J 3323—connects to prime and drain line;
Port K 3324—reservoir infusate input;
Port M 3325—infusate in from the infusate reservoir;
Port N 3326—dialysate flow into sorbent.

In one implementation, a tube segment, formed as a pathway molded into the manifold structure 3300, connects the fluid flow of heparin 3314, entering via Port D 3318, to the fluid flow of blood, entering via Port C 3317. The combined heparin and blood flow through port 3317*a*, via pump segment 3301, and into port 3317*b* of the manifold 3300. A pressure transducer 3305 is in physical communication with a membrane, formed in the manifold structure 3300, which, in turn, passes the blood and heparin fluid through Port A 3315. Fluid flow out of the manifold 3300 at Port A 3315 passes through dialyzer 3330, which is external to the manifold 3300. The dialyzed blood passes back into the manifold 3300 through Port G 3321 and into a segment 3307, formed as a pathway molded into the manifold structure 3300 that is in physical communication with a pressure transducer. Fluid then passes from the segment through Port H 3322 and into a patient return line.

Separately, dialysis fluid enters the manifold 3300 from a reservoir via Port E 3319. Fluid in the reservoir has infusate in it, which first enters the manifold 3300 via Port M 3325, passes through a segment, formed as a pathway molded into the manifold structure 3300, through another port 3325*a*, through a segment 3302 in communication with a pump, and back into the manifold 3300 via port 3325*b*. The infusate passes through a segment, formed as a pathway molded into the manifold structure 3300, and out the manifold 3300 at Port K 3324, where it passes into the reservoir. The dialysis fluid which entered the manifold via Port E 3319 passes through a segment, formed as a pathway molded into the manifold structure 3300, through another port 3319a, through a segment 3303 in communication with a pump, and back into the manifold 3300 via port 3319b.

The dialysate fluid passes into a segment, formed as a pathway molded into the manifold structure 3300, which is in physical communication with two-way valve 3311. A segment, formed as a pathway molded into the manifold structure 3300, passes the dialysate fluid to two-way valve 3313. The segment is in physical communication with pressure transducer 3308 and optional temperature sensor 3310. The dialysate fluid passes out of the manifold 3300 through Port F 3320, and into a line that passes into the dialyzer 3330.

A line out of the dialyzer 3330 passes fluid back into the manifold 3300 through Port B 3316 and into a segment, formed as a pathway molded into the manifold structure 3300, that is in physical communication with two-way valve 3311, two-way valve 3312, and a pressure transducer 3306. The used dialysate fluid passes out of the manifold 3300 through port 3326b, through segment 3304 in communication with a pump, and back into the manifold via port 3326a. A segment in fluid communication with port 3326a is in physical communication with pressure transducer 3309 and passes fluid through Port N 3326 and to a sorbent regeneration system.

Figure 3:
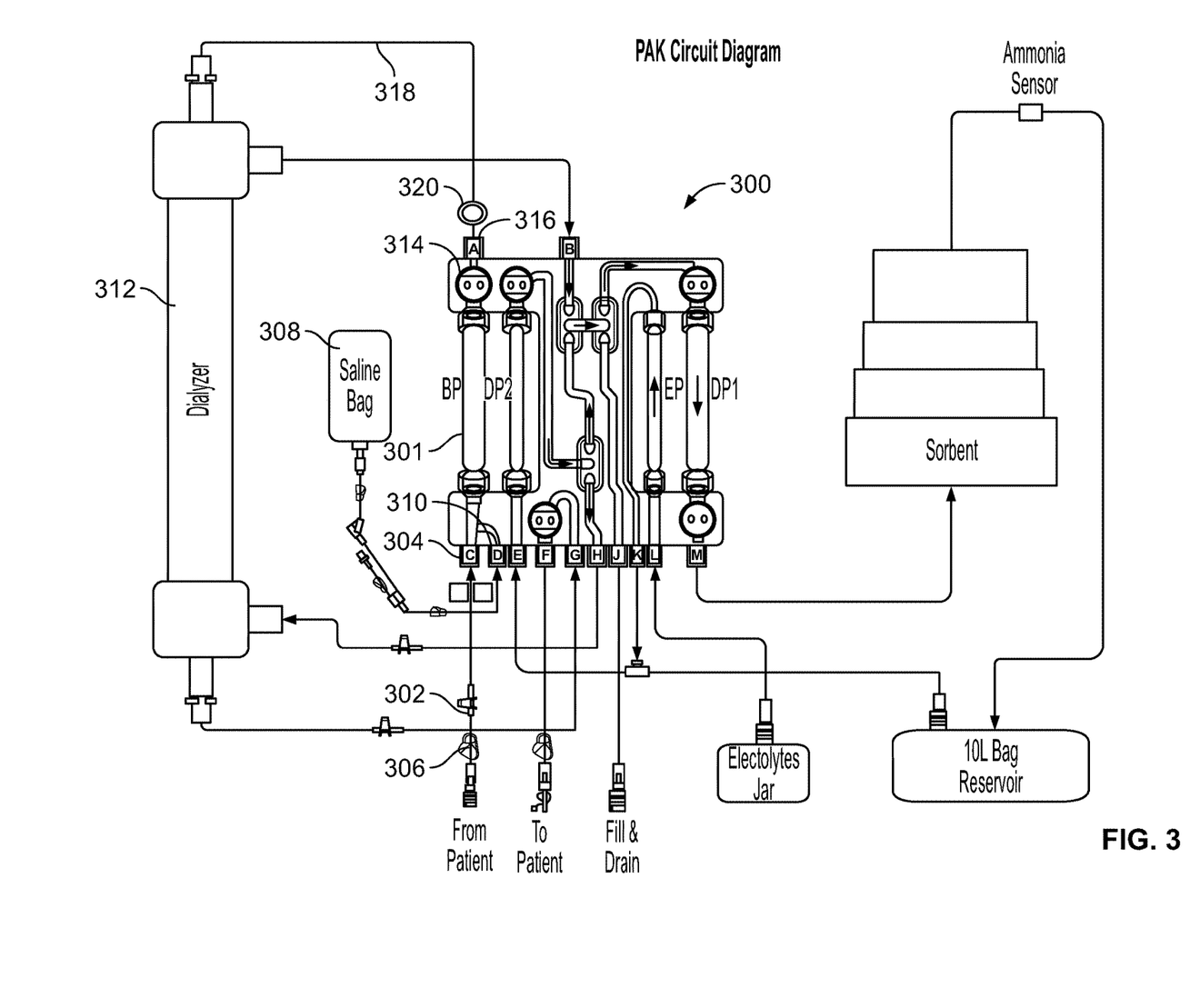
FIG. 3 is a schematic of an exemplary manifold employed in an extracorporeal blood processing system used for conducting hemodialysis and hemofiltration according to some implementations of the present specification.

FIG. 3 is a schematic of an exemplary manifold employed in an extracorporeal blood processing system used for conducting hemodialysis and hemofiltration according to some implementations of the present specification. As shown in FIG. 3, a blood circuit connection between the patient and the dialysis system is maintained via tubular segment 302, which connects to the manifold 300 at port C 304 and the patient at connection point 306. At arterial blood pump flow rates in the range of 200 ml per minute to 500 ml per minute, if an occlusion is present in arterial line 302, a pressure drop may be observed at or proximate to point 314 in the manifold proximate to port A 316 which carries blood to the dialyzer 312 during active operation of the hemodialysis system. In an implementation, blood flow pressure is measured at point 314 or 318 which is positioned just before the patient's blood enters the dialyzer 312. The measured pressure is correlated with or compared to a pre-defined arterial pressure and an alarm is configured to be triggered in cases of skewed correlation results.

Abrupt changes in pressure at points 314 and/or 318 may be used to provide an indication of alarm. In an implementation, an abrupt change in arterial blood pressure is observed if the arterial line carrying blood from a patient to port C 304 is clamped. Typically, the blood pressure is negative at point C 304 which is the point of entry of the blood into the manifold 300, and is positive upon exiting at port A 316. In the case of an occlusion in the arterial line 302, an abrupt drop in blood pressure is observed at port A 316. In various implementations, a pressure sensor is employed to measure the sudden pressure drop and cause an alarm to trigger in response.

In an implementation, a pressure sensor 320 is employed in the hemodialysis system as shown in FIG. 3 to trigger a negative pressure alarm due to an occlusion anywhere in the arterial line or tube segment carrying blood from the patient to the dialyzer 312. In implementations, the pressure sensor 320 is positioned proximate point 314 (corresponds to point 3305 of FIG. 2) in the manifold proximate port A 316 which carries blood to the dialyzer 312. Effectively, the pressure sensor 320 is positioned at an output point of a blood pump that acts on the tube segment 301 between point 314 and the arterial line 302 (also referred to as a "patient out line").

In an implementation, a slope of pressure change can be used to determine the type, extent, and severity of the alarm. A threshold drop of 325 mm Hg pressure over 3 seconds observed at port A 316 indicates an arterial occlusion at all blood flow rates and causes an alarm to trigger. In another implementation, during a saline bolus or flushing operation where saline is introduced via saline bag 308 into Port D 310 of FIG. 3, a threshold drop of 450 mm Hg pressure over 3 seconds at port A 316 indicates an arterial occlusion at all blood flow rates and causes an alarm to trigger.

The pressure signal data, generated by the pressure sensor 320, is read into a controller that implements a process of analyzing pressure signal data to detect and alarm a sudden drop in pressure due to occlusion—at arterial blood pump flow rates extending from 100 ml per minute to 600 ml per min and preferably at flow rates in the range of 200 ml per minute to 500 ml per minute. It should be noted that pressure signal data is generated at a fast rate (by the pressure sensor 320) with varying magnitude and having a plurality of positive and negative swings even though an aggregated resulting signal may look stable. Therefore, to condition the pressure signal data by averaging and using the average for detecting a sudden drop in pressure is less optimal since the averaging creates a delay that in turn causes an unwanted delay in alarm activation.

Figure 8:
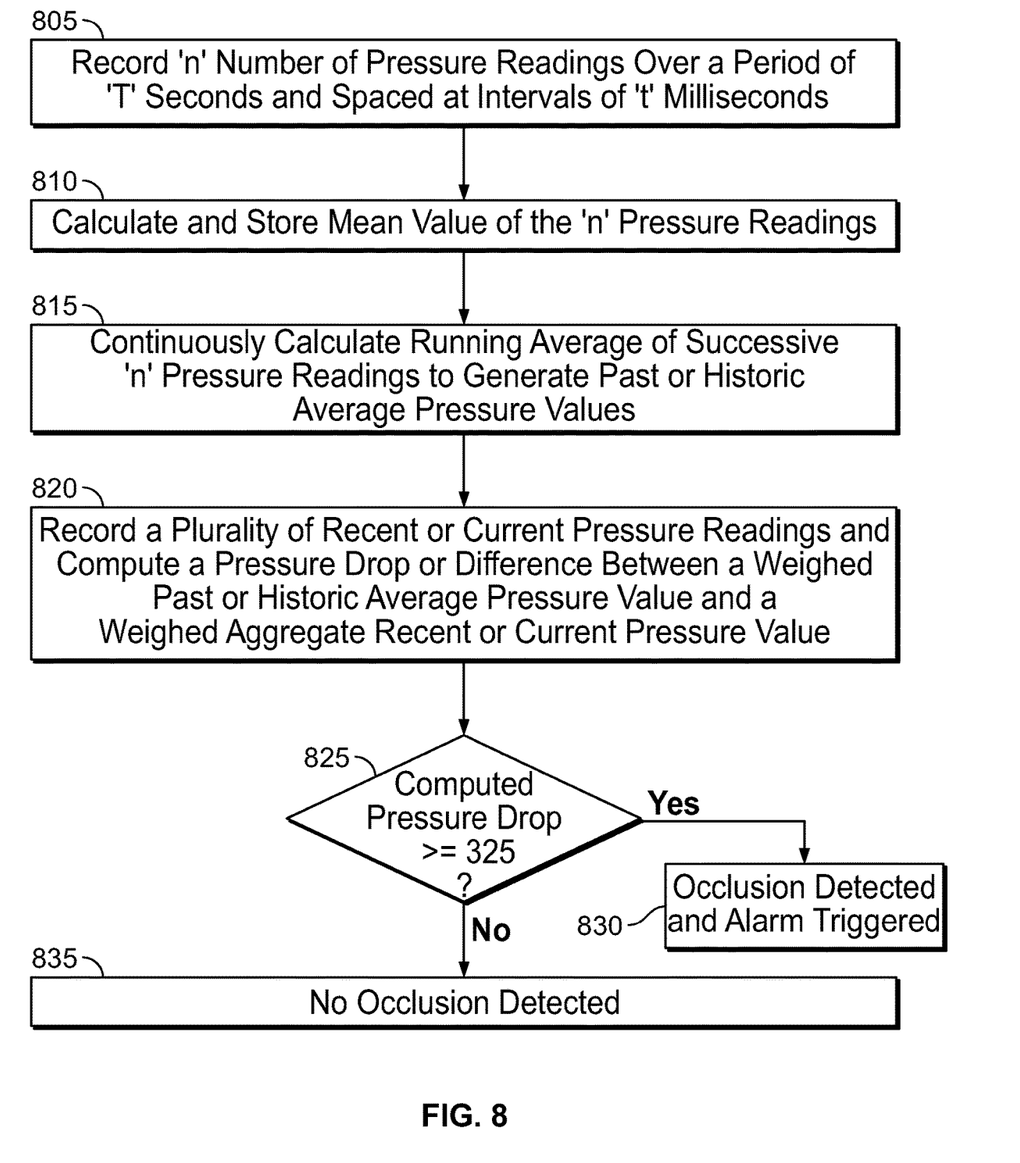
FIG. 8 is a flowchart illustrating a plurality of steps of an occlusion detection method in an arterial patient out line of a hemodialysis system of the present specification.

FIG. 8 is a flowchart illustrating a method of analyzing pressure signal data, generated by the pressure sensor 320 of FIG. 3 or 3305 of FIG. 2, to detect and alarm a sudden drop in pressure due to occlusion in an arterial patient line of a hemodialysis system. It should be appreciated that this method is implemented by a controller comprising at least one processor and a non-transient memory having a plurality of programmatic instructions stored therein. The pressure sensors, which may be located in a dialysis machine, are in physical communication with a diaphragm or valve structure positioned in the manifold at 320 of FIG. 3 or 3305 of FIG. 2. The pressure sensor senses variations in pressure at the aforementioned points and communicates, in real-time, to a non-transient memory. The processor retrieves the generated pressure data from non-transient memory and executes the plurality of programmatic instructions embodying the process described below.

At step 805, 'n' number of pressure readings are recorded into the non-transient memory over a period of 'T' seconds and spaced at intervals of T milliseconds. In some implementations, n=16, T=8 seconds and t=500 milliseconds. In other words, 16 pressure readings are recorded every 500 milliseconds (or twice a second) over a period of 8 seconds. It should be appreciated that n can be in a range of 4 to 160, T can be in a range of 2 to 80 seconds and t can be in a range of 125 to 5000 milliseconds, or any increment therein.

Figure 9:
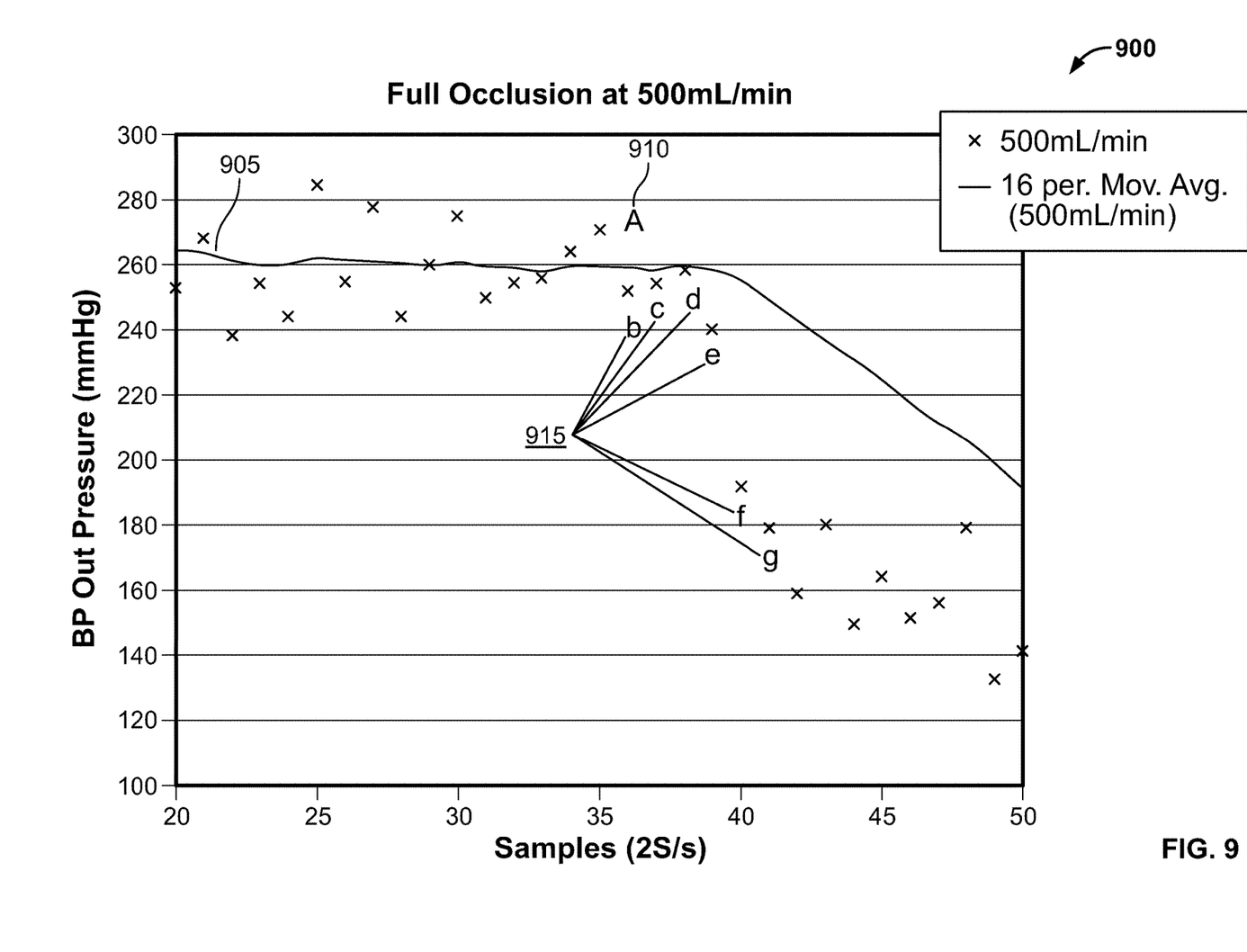
FIG. 9 illustrates a graphical representation of continuously recorded running averages of successive 'n' pressure readings at a predetermined flow rate.

At step 810, a mean or an average pressure value is calculated and stored for the recorded 'n' pressure readings. At step 815, a running average of successive 'n' pressure readings, is calculated continuously to generate and store past or historic average pressure values over a course of operation of the hemodialysis system. FIG. 9 is a graph 900 illustrating a curve 905 plotted for continuously recorded running averages of successive 'n' pressure readings at an exemplary flow rate of 500 ml per minute. Each running average is determined by obtaining the most recent 'n' readings and calculating the average of those readings. Therefore the running average at time T+1 will differ from the running average at time T by having incorporated the latest pressure reading (at time T+1) and eliminated the oldest pressure reading (at time T-n, or 'n' readings ago).

To detect occlusion, at step 820, a plurality of recent or current pressure readings are recorded. Each of these current readings are weighed and aggregated or summed up to obtain a weighed aggregate recent or current pressure value. In an implementation, 6 recent or current pressure readings are recorded and each of these 6 recent or current pressure readings is weighed using a first weight. In an implementation, the first weight is 1. Thereafter, a pressure drop or difference is computed between a weighed past or historic average pressure value and the weighed aggregate recent or current pressure value. In implementations, the past or historic average pressure value is weighed using a second weight. In one implementation, the second weight is 6. Referring back to FIG. 9, value 'A' 910 corresponds to recorded past or historic average pressure value. Points 915 (represented as values b, c, d, e, f and g) correspond to a plurality of, such as 6, recent or current pressure readings. Thus, in accordance with step 820, the pressure drop or difference is calculated as follows:

Pressure drop or difference=$(w_1 \times A)-(w_2 b+w_3 c+w_4 d+w_5 e+w_6 f+w_7 g)$, where A is a running average of n historical pressure values, variables b, c, d, e, f, and g are the most recently sensed individual pressure values, and $w_1$, $w_2$, $w_3$, $w_4$, $w_5$, $w_6$, $w_7$ are weighting factors, with $w_1$ being in a range of 3 to 10, preferably 6, and $w_2$, $w_3$, $w_4$, $w_5$, $w_6$, and $w_7$ being in a range of 1 to 5, preferably 1.

For example, upon initiating operation and throughout a dialysis procedure, the pressure sensor senses, and transmits to the non-transient memory, a plurality of pressure values, 1 . . . m, where m represents the most recent pressure value. A first variable, A, is calculated using a subset of those pressure readings. In one implementation, the controller determines A by obtaining n pressure values, of the entire m pressure value dataset, where n is in a range of 4 to 120 values, preferably 10 to 20 values, and more preferably 16 values. Additionally, the most recent value in the n dataset is less recent than m. Stated differently, the n dataset of pressure values includes 10 to 20 values where the most recent value is equal to m-x, where 'x' is in a range of 3 to 10, preferably 5. Consequently, the running average, A, is calculated using a dataset of n values which comprise recent pressure values, but not the 'x' most recent data values, thereby constituting a historical running average. This variable, A, is then weighted by a first weighting factor. Because A is calculated based on historical data, and not the most recent 'x' sensed values, it can be calculated and stored while the most recent 'x' sensed values are being concurrently generated, thereby ensuring that 'A' is readily available for use and not delaying the occlusion detection process and generation of an alarm.

Concurrently, some or all of the 'x' most recent data values are used to calculate the values represented above as b, c, d, e, f, and g. Each of these values is weighted by a weighting factor, such as 1, and then summed. This sum is then subtracted from A, as shown in the equation above, to yield the pressure difference. This pressure difference value is referred to as an occlusion indicator value. It should be appreciated that this occlusion indicator value may be determined using other functions than subtraction, including logarithmic, division, multiplication, addition, and other mathematical functions.

At step 825, the pressure drop or difference is compared against a pre-defined threshold pressure difference value. In one implementation, during a hemodialysis operation, the threshold pressure difference value is 325 mm Hg for all flow rates of the blood pump. In another implementation, during a saline bolus operation, the threshold pressure difference value is 450 mm Hg pressure for all saline flow rates. Accordingly, at step 830, if the occlusion indicator value is greater than or equal to 325 mm Hg, the controller is programmed to identify this drop as being indicative of an occlusion and therefore initiate an auditory or visual occlusion alarm, along with terminating or suspending the dialysis process. If, at step 835, the pressure difference is less than 325 mm Hg, then the controller is programmed to keep operating and not trigger an auditory or visual alarm because this difference is not attributable to an occlusion. The same process applies with a saline bolus operation and a threshold pressure difference of 450 mm Hg. It should be appreciated that since the recent or current pressure readings are aggregated, raw sensed data, and not subjected to the averaging process of variable 'A' (which is concurrently done on historical data), this leads to a faster response alarm. It should also be appreciated that the controller may also be programmed to initiate an alarm, or suspend or terminate a dialysis procedure, if the occlusion indicator value is less than or equal to a predefined threshold number, such as 325 mmHg or 450 mmHg. In one implementation, the predefined threshold number is in a range of 200 mmHg to 450 mmHg and any increment therein.

The occlusion detection method of FIG. 8 reliably identifies an occlusion with minimal false positives or negatives and works for flow rates extending from 100 ml/minute to 600 ml/min (preferably 200-500 ml/minute). The method also handles or accounts for pressure variance during flow (which is not attributable to an occlusion but which conventional hemodialysis systems mistake for an occlusion), which could range up to 50 mm Hg.

Figure 10:
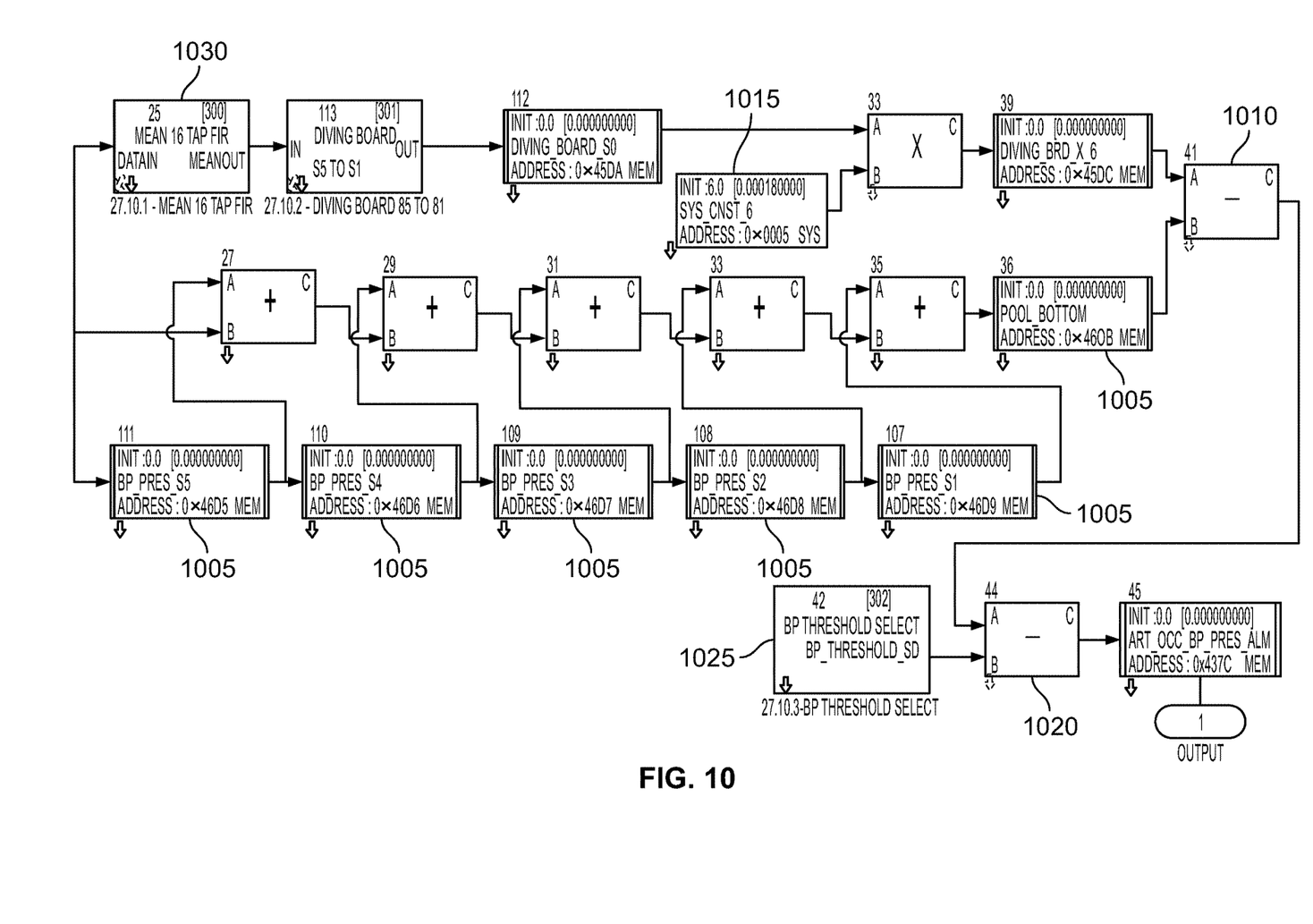
FIG. 10 is a block diagram illustration of the occlusion detection method of FIG. 8 in accordance with one implementation.

FIG. 10 is a block diagram illustration of the occlusion detection method of FIG. 8 in accordance with one implementation. As shown in FIG. 10, each of the six registries or memory blocks 1005 respectively store or record present or current pressure values. Each of the pressure values at the blocks 1005 are weighed by a weight, such as 1, and summed up to generate a weighed aggregate recent or current pressure value. At block 1010, a pressure drop or difference is calculated between a weighed past or historic average pressure value ('A') and the weighed aggregate recent or current pressure value. Block 1030 stores a historic or past mean or average pressure value that in an implementation is calculated for 16 pressure readings over a period of 8 seconds and spaced at 500 milliseconds. The past or historic average pressure value is weighed, using a weight of 6, as represented in block 1015. Finally, the pressure difference is compared, at block 1020, against a predefined threshold pressure difference value (represented in block 1025) to detect occlusion and resultantly trigger an alarm.

Figure 4A:
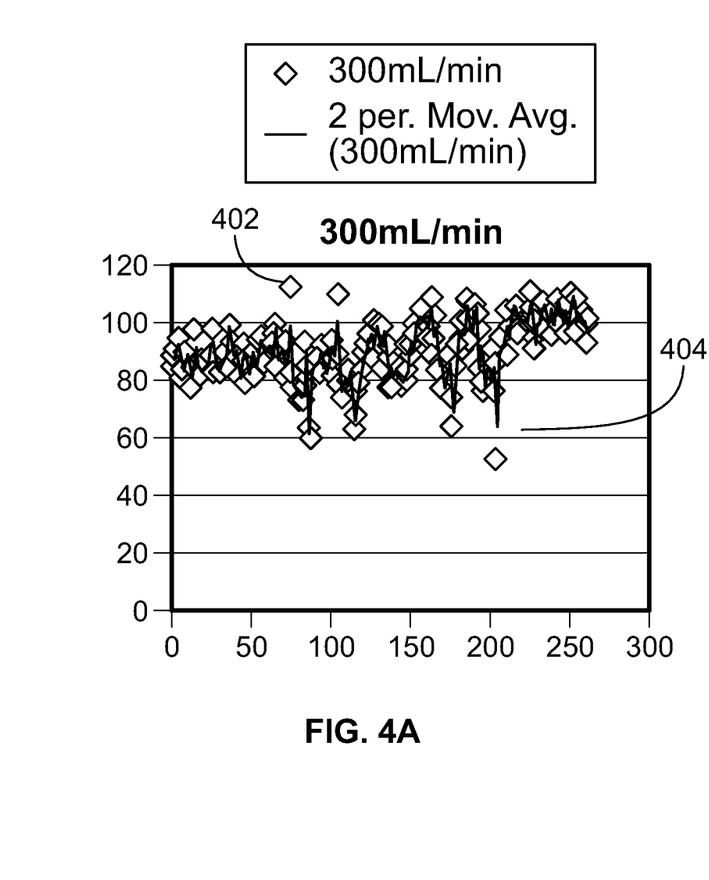
FIG. 4A illustrates a graphical representation of moving averages of multiple blood pressure values corresponding to a blood flow rate of 300 mL/min over a predetermined period of time.

FIG. 4A illustrates a graphical representation of moving averages of multiple blood pressure values corresponding to a blood flow rate of 300 mL/min over a predetermined period of time. Point 402 represent the fluctuation in blood pressure values. Line 404 represents the moving average of pressure values calculated with an interval value of two.

Figure 4B:
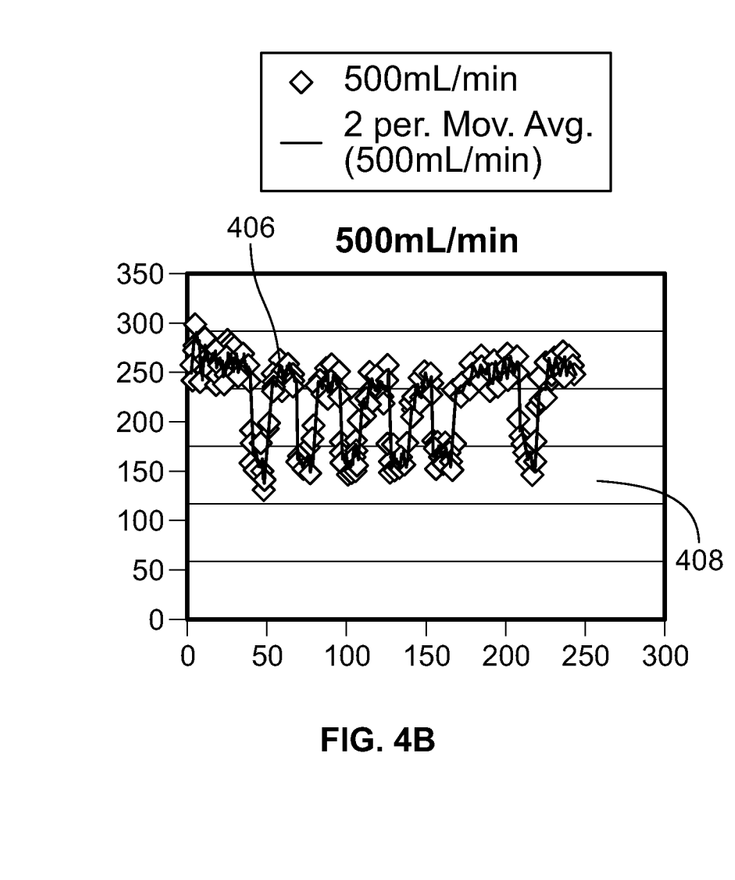
FIG. 4B illustrates a graphical representation of moving averages of multiple blood pressure values corresponding to a blood flow rate of 500 mL/min over a predetermined period of time.

FIG. 4B illustrates a graphical representation of moving averages of multiple blood pressure values corresponding to a blood flow rate of 500 mL/min over a predetermined period of time. Point 406 represent the fluctuation in blood pressure values. Line 408 represents the moving average of pressure values calculated with an interval value of two.

Figure 5:
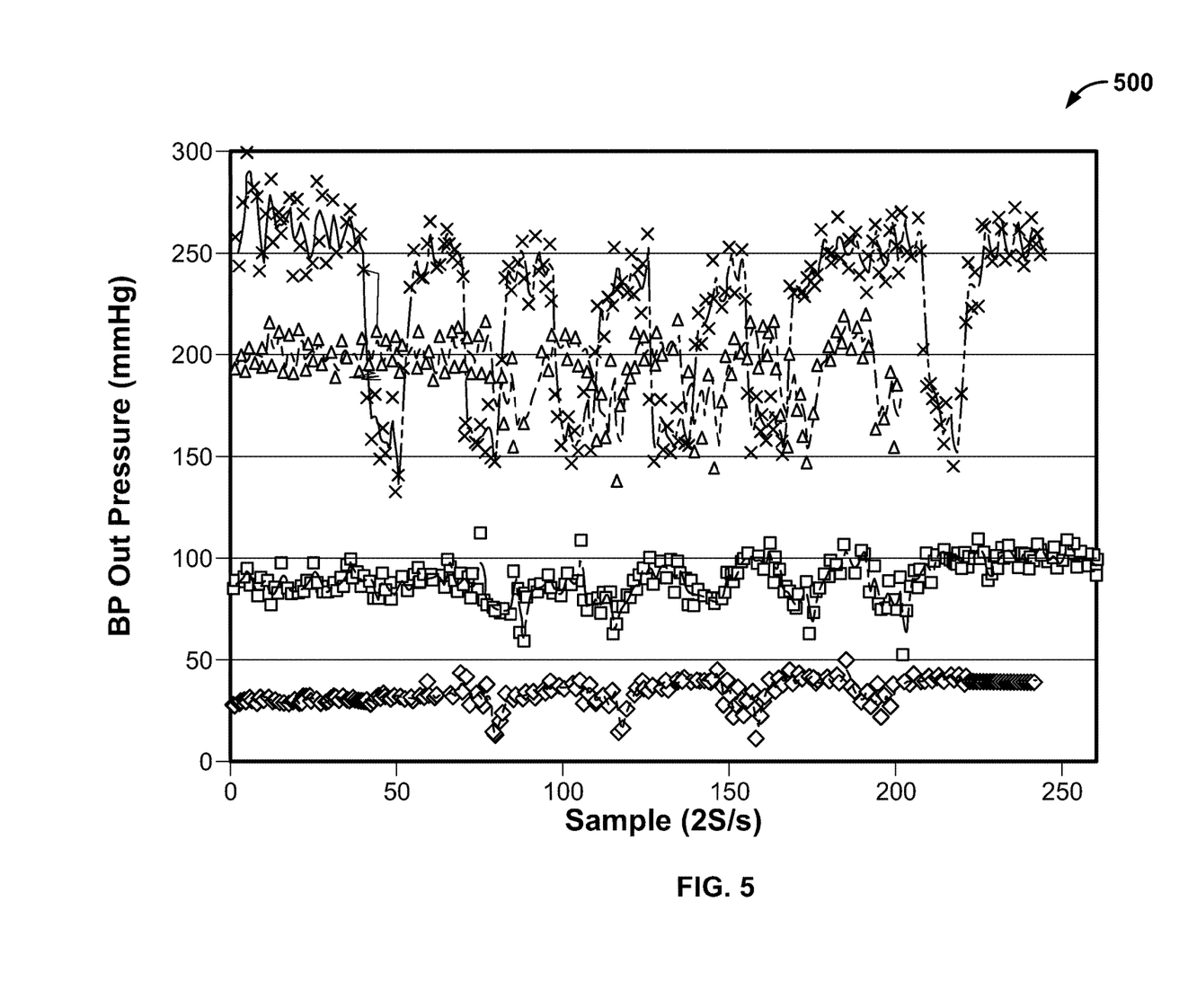
FIG. 5 illustrates another graphical representation of moving averages of multiple blood pressures values corresponding to predetermined blood flow rates over a predetermined period of time.

FIG. 5 illustrates another graphical representation 500 of moving averages of multiple blood pressures values corresponding to predetermined blood flow rates over a predetermined period of time.

Figure 6:
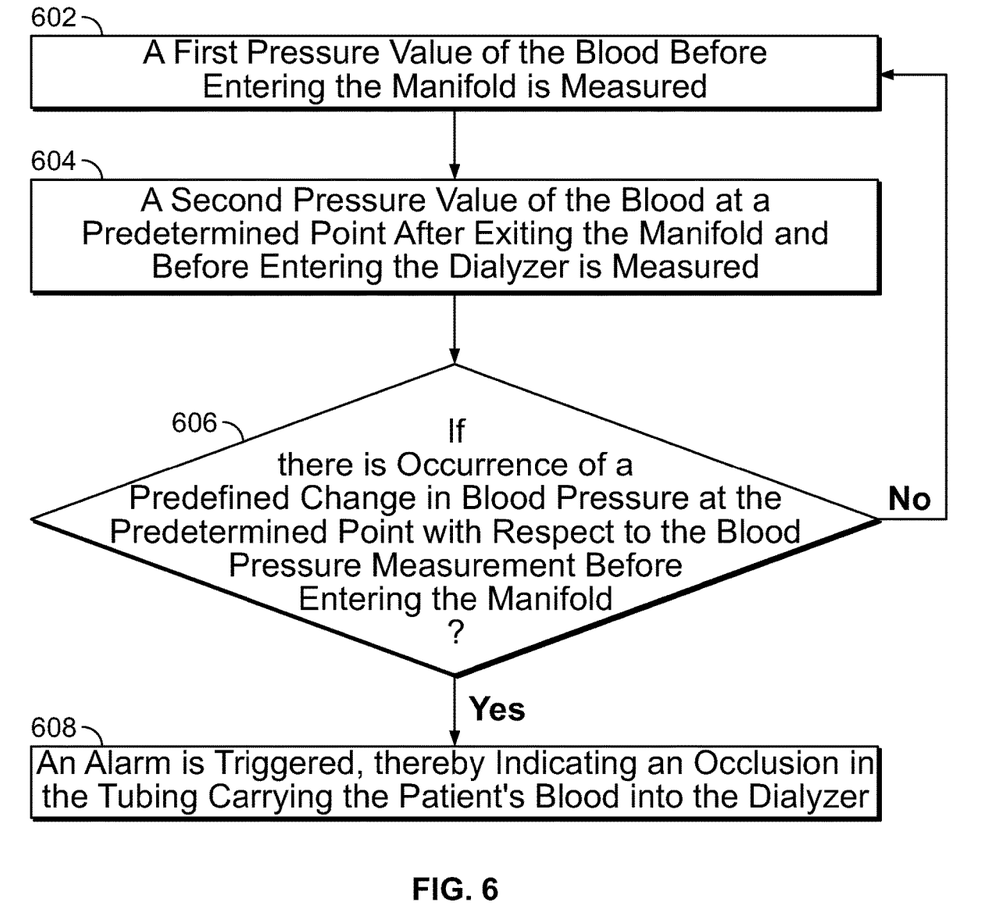
FIG. 6 is a flowchart illustrating a method for detecting an occlusion in a tubing directing a patient's blood into a dialyzer in a hemodialysis system, in accordance with an implementation of the present specification.

FIG. 6 is a flowchart illustrating a method for detecting an occlusion in a tubing carrying a patient's blood into a dialyzer in a hemodialysis system, in accordance with an implementation of the present specification. Described with reference to FIG. 3, the blood from the patient's body is pumped into the dialyzer via a manifold defining a blood flow path. At step 602 a first pressure value of the blood before entering the manifold is measured. At step 604 a second pressure value of the blood at a predetermined point after exiting the manifold, preferably point 3305 of FIG. 2 or 314 of FIG. 3, and before entering the dialyzer is measured. At step 606 it is determined if there is occurrence of a predefined change, as described above, in blood pressure at the predetermined point with respect to the blood pressure measurement before entering the manifold. At step 608 an alarm is triggered upon occurrence of the predefined change in blood pressure, thereby indicating an occlusion in the tubing carrying the patient's blood into the dialyzer.

Figure 7:
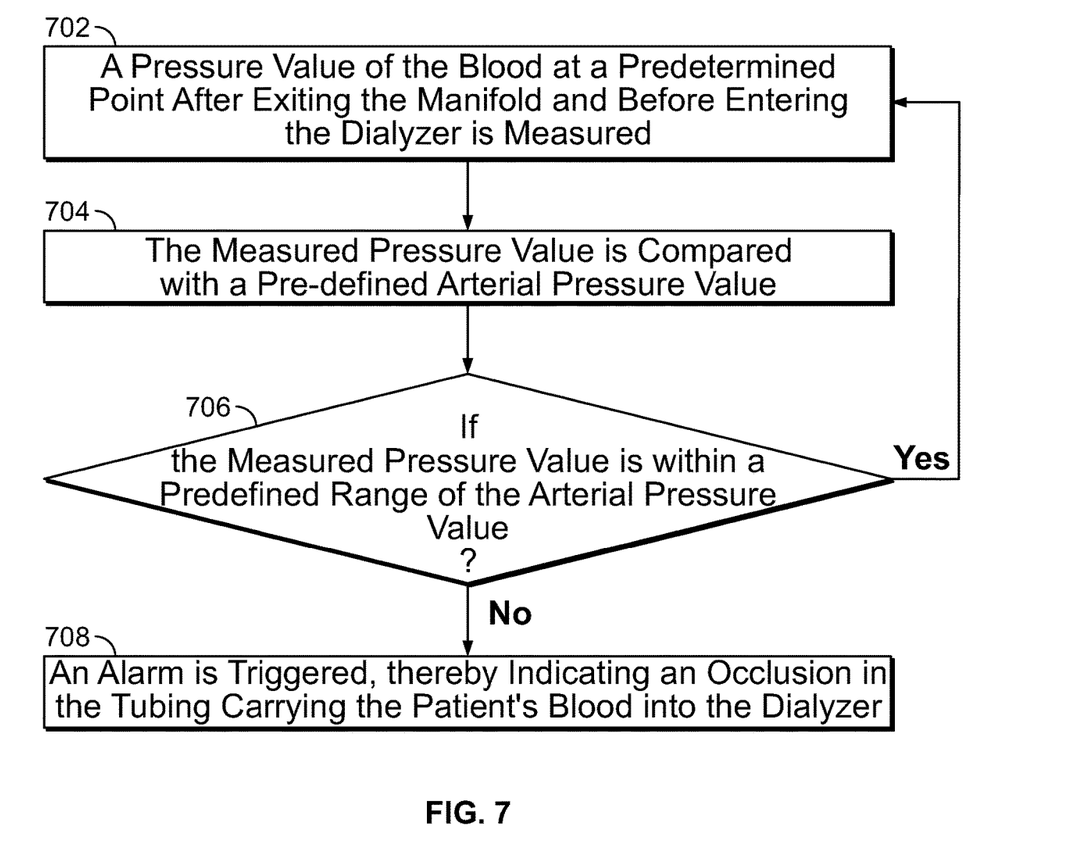
FIG. 7 is a flowchart illustrating another method for detecting an occlusion in a tubing directing a patient's blood into a dialyzer in a hemodialysis system, in accordance with an implementation of the present specification.

FIG. 7 is a flowchart illustrating another method for detecting an occlusion in a tubing carrying a patient's blood into a dialyzer in a hemodialysis system, in accordance with an implementation of the present specification. At step 702 a pressure value of the blood at a point after exiting the manifold and before entering the dialyzer is measured, preferably point 3305 of FIG. 2 or 314 of FIG. 3. At step 704, a sum of measured pressure values are compared with an average arterial pressure value, as described above. At step 706, it is determined if the difference in pressure values is within a predefined range. At step 708 if the measured pressure value is not within a predefined range of the arterial pressure value an alarm is triggered, thereby indicating an occlusion in the tubing carrying the patient's blood into the dialyzer.

The above examples are merely illustrative of the many applications of the system of present invention. Although only a few implementations of the present invention have been described herein, it should be understood that the present invention might be embodied in many other specific forms without departing from the spirit or scope of the invention. Therefore, the present examples and implementations are to be considered as illustrative and not restrictive, and the invention may be modified within the scope of the appended claims.

We claim:

1. A dialysis system comprising:
a flexible tube in fluid communication with a fluid port;
a pressure sensor in physical communication with the flexible tube, wherein the pressure sensor is configured to generate and transmit values indicative of pressure levels in the flexible tube;
a non-transient memory in data communication with the pressure sensor and configured to store the values;
at least one pump in fluid contact with the flexible tube and configured to pump fluid through the tube; and
a controller in data communication with the pressure sensor, the non-transient memory, and the at least one pump, wherein the controller is configured to execute a plurality of programmatic instructions in order to:
receive the values;
determine a first function of n values, where n is a subset of the values;
determine a second function of m values, where m is a subset of the values and where m<n;
apply a function to the first function of n values and the second function of m values to generate an occlusion indicator value; and
based upon the occlusion indicator value, determine if an alarm should be triggered.

2. The dialysis system of claim 1 further comprising a housing that encloses the controller, the at least one pump, and the pressure sensor, wherein the housing is adapted to detachably receive a manifold and wherein the manifold comprises the flexible tube.

3. The dialysis system of claim 1 further comprising a dialyzer in fluid communication with the fluid port of the flexible tube.

4. The dialysis system of claim 3 wherein the pressure sensor is positioned between the fluid port and the dialyzer.

5. The dialysis system of claim 1 wherein n is in a range of 10 to 20 pressure values.

6. The dialysis system of claim 1 wherein m is in a range of 3 to 10 pressure values.

7. The dialysis system of claim 1 wherein the first function is an average of the n values, wherein the second function is a sum of the m values, and wherein the m values include values that are sensed more recently than values in the average of n values.

8. The dialysis system of claim 1 wherein the first function is an average of the n values, wherein the second function is a sum of the m values, and wherein the m values include values sensed later in time than values in the n values.

9. The dialysis system of claim 1 wherein the controller is configured to execute a plurality of programmatic instructions in order to apply a weight to the first function of n values.

10. The dialysis system of claim 9 wherein the weight is in a range of 3 to 10.

11. The dialysis system of claim 1 wherein the controller is configured to execute a plurality of programmatic instructions in order to apply a weight to each value in the m values.

12. The dialysis system of claim 11 wherein the weight is in a range of 1 to 5.

13. The dialysis system of claim 1 wherein the function is a difference between a result of the first function and a result of the second function.

14. The dialysis system of claim 13 wherein the controller is configured to determine whether the alarm should be triggered when the occlusion indicator value is greater than or equal to a predefined threshold number.

15. The dialysis system of claim 14 wherein the predefined threshold number is in a range of 200 to 450 mmHg.

16. The dialysis system of claim 13 wherein the controller is configured to determine whether the alarm should be triggered when the occlusion indicator value is less than or equal to a predefined threshold number.

17. The dialysis system of claim 16 wherein the predefined threshold number is in a range of 200 to 450 mmHg.

18. The dialysis system of claim 1 further comprising a manifold comprising a blood inlet port and a blood outlet port, wherein the flexible tube is positioned between the blood inlet port and the blood outlet port.

19. The dialysis system of claim 18 wherein the pressure sensor is positioned proximate the blood outlet port.

20. The dialysis system of claim 18 wherein the first function is an average of then values and the second function is a sum of the m values and wherein the function generates a difference between a result of the first function and a result of the second function to generate the occlusion indicator value.

* * * * *